United States Patent [19]

Ogawa

[11] Patent Number: 6,047,204
[45] Date of Patent: Apr. 4, 2000

[54] METHOD OF AND APPARATUS FOR STORING DIAGNOSTIC IMAGE INFORMATION

[75] Inventor: Eiji Ogawa, Kanagawa-ken, Japan

[73] Assignee: Fuji Photo Film Co., Ltd., Kanagawa-ken, Japan

[21] Appl. No.: 08/960,063

[22] Filed: Oct. 29, 1997

[30] Foreign Application Priority Data

Oct. 31, 1996 [JP] Japan .................................. 8-289728

[51] Int. Cl.[7] ...................................................... A61B 5/05
[52] U.S. Cl. ........................................................ 600/407
[58] Field of Search ................................... 600/407, 410, 600/300, 117, 118, 109; 382/128, 294, 295, 305, 306; 345/514; 395/117; 378/165; 128/920, 923

[56] References Cited

U.S. PATENT DOCUMENTS 4,969,049  11/1990  Mitani et al. ............................ 358/296
5,584,293  12/1996  Darrow et al. ........................ 128/653.2
5,644,765   7/1997  Shimura et al. ......................... 395/615
5,779,634   7/1998  Ema et al. ............................... 600/407
5,878,746   3/1999  Lemelson et al. ....................... 600/407

Primary Examiner—Brian L. Casier
Attorney, Agent, or Firm—Sughrue, Mion, Zinn, Macpeak & Seas, PLLC

[57] ABSTRACT

When storing, in a storage medium, diagnostic image information representing a diagnostic image which is displayed on an image display system and on the basis of which a diagnosis is made, information on the viewing condition of the diagnostic image displayed on the image display system used in making the diagnosis is stored in the storage medium together with the diagnostic image information. The information on the viewing condition of the diagnostic image includes at least one of the condition of the image processing which is additionally carried out when the diagnostic image used in making the diagnosis is displayed by the image displaying system, the displaying properties of the display system itself and the condition of environment in which the system stands.

16 Claims, 1 Drawing Sheet

METHOD OF AND APPARATUS FOR STORING DIAGNOSTIC IMAGE INFORMATION

BACKGROUND OF THE INVENTION

1. Field of the Invention

This invention relates to a method of and apparatus for storing diagnostic image information, and more particularly to an improvement in supplementary information which is stored attached to diagnostic image information.

2. Description of the Related Art

An image is often stored by storing an image signal representing the image in a storage medium such as a magnetic disc, an optical disc or the like.

In the medical field, a diagnostic image of a patient is taken by a CR system, a CT system or the like, and the diagnostic image is generally recorded on photographic film or the like for diagnosis. At the same time, the diagnostic image is stored in various storage media as a digital image signal or the like for later use, for instance, for inspecting change with time of the condition of the patient. Further such diagnostic image information is generally stored together with supplementary information such as information for identifying the patient, e.g., name, age, sex, ID number and the like of the patient, information for identifying the image, e.g., the number of the image, the date of taking the image, and the like, information on the taking condition, e.g., the kind of the system by which the image was taken, the direction of taking the image, the kind of the contrast agent and the like, and parameters used in processing the image.

Further the diagnostic image information is not only reproduced as an image recorded on a photographic film or the like but also often used in diagnosis as an image displayed on a display system such as a CRT or the like. Displaying the image on a display system is advantageous over recording the image on a photosensitive material in that the image can be output in a time shorter than when the image is recorded on the photosensitive material and a disadvantage that the photosensitive material is consumed in vain in the case the user carries out an image processing on the basis of trial and error can be avoided.

However the quality of the image displayed on the display system is affected, for instance, by properties of the display system such as the degree of deterioration of the system, the environment in which the system stands and the image processing which the user added for the purpose of diagnosis.

Accordingly, if a doctor makes a diagnosis on the basis of a diagnostic image displayed under a certain viewing condition, the same result cannot be always obtained when the same doctor makes a diagnosis later on the basis of the same diagnostic image displayed on the same display system under a different viewing condition. This can result in an event that the base of diagnosis in the first diagnosis cannot be known.

SUMMARY OF THE INVENTION

In view of the foregoing observations and description, the primary object of the present invention is to provide a method of and an apparatus for storing a diagnostic image information which enable a diagnostic image which is displayed on a display image and used in a diagnosis to be faithfully reproduced later with the same image quality, impression and the like.

In accordance with the present invention, information on the viewing condition of a diagnostic image displayed on an image display system used in a diagnosis is stored in a storage medium together with the diagnostic image information representing the diagnostic image.

That is, in accordance with one aspect of the present invention, there is provided a method of storing, in a predetermined storage medium, diagnostic image information representing a diagnostic image which is displayed on an image display system and on the basis of which a diagnosis is made, characterized in that information on the viewing condition of the diagnostic image displayed on the image display system used in making said diagnosis is stored in the predetermined storage medium together with the diagnostic image information.

The information on the viewing condition of the diagnostic image includes, for instance, the condition of the image processing which the user added when displaying said diagnostic image, the displaying properties of the display system itself and the condition of environment in which the system stands. More specifically, the condition of the image processing which the user added includes a gradation processing, a frequency processing, an enlargement/contraction processing, a gradation correction processing of the image display system and the like. The displaying properties include a maximum brightness, gradation, chromaticity, sharpness, noise characteristics and the like. The condition of environment includes illuminance on the screen of the image display system, chromaticity of the environmental light, the distance between the screen surface and the viewer, and the like. The information on the viewing condition may be expressed in direct values in the term of unit inherent to each information or in alternative values corresponding thereto.

The image processing which the user added means an image processing which the user carries out on the basis of trial and error viewing the image displayed on the display system unlike the image processing carried out on the input image information under predetermined conditions or a preset image processing carried out on the basis of the image information.

The image processing conditions can be obtained by detecting a parameter for each processing. The displaying properties can be detected by causing the image display system to display a reference pattern image and monitoring the reference pattern image from the exterior. The condition of environment can be detected by an illuminance detecting means such as a photodiode disposed on or near the screen surface to detect illuminance on the screen of the image display system.

In accordance with another aspect of the present invention, there is provided a diagnostic image information storing apparatus comprising an image displaying means which displays a diagnostic image and a storage means which stores, in a predetermined storage medium, diagnostic image information representing the diagnostic image displayed by the image displaying means, wherein the improvement comprises a viewing condition detecting means which detects information on the viewing condition of the diagnostic image displayed by the image displaying means, a storage instruction signal generating means which generates a storage instruction signal, which commands that information is to be stored, in response to a signal representing that the image currently displayed by the image displaying means is used for a diagnosis, and an attaching means which attaches the information on the viewing condition detected by the viewing condition detecting means upon generation of the storage instruction signal to the diagnostic image information, said storage means storing the diagnostic image information attached with the information on the viewing condition in said storage medium.

In accordance with the present invention, the image on the basis of which a diagnosis is made can be reproduced later with the same image quality, impression and the like since the diagnostic image information is stored together with the information on the viewing condition which affects the quality of the image displayed by the image displaying device. Accordingly, judgment upon the diagnosis can be confirmed later and fluctuation in the result of diagnosis due to change in the viewing condition can be avoided.

BRIEF DESCRIPTION OF A DRAWING

FIG. 1 is a diagram showing a diagnostic image information storing apparatus in accordance with an embodiment of the present invention.

DESCRIPTION OF THE PREFERRED EMBODIMENT

Figure 1:
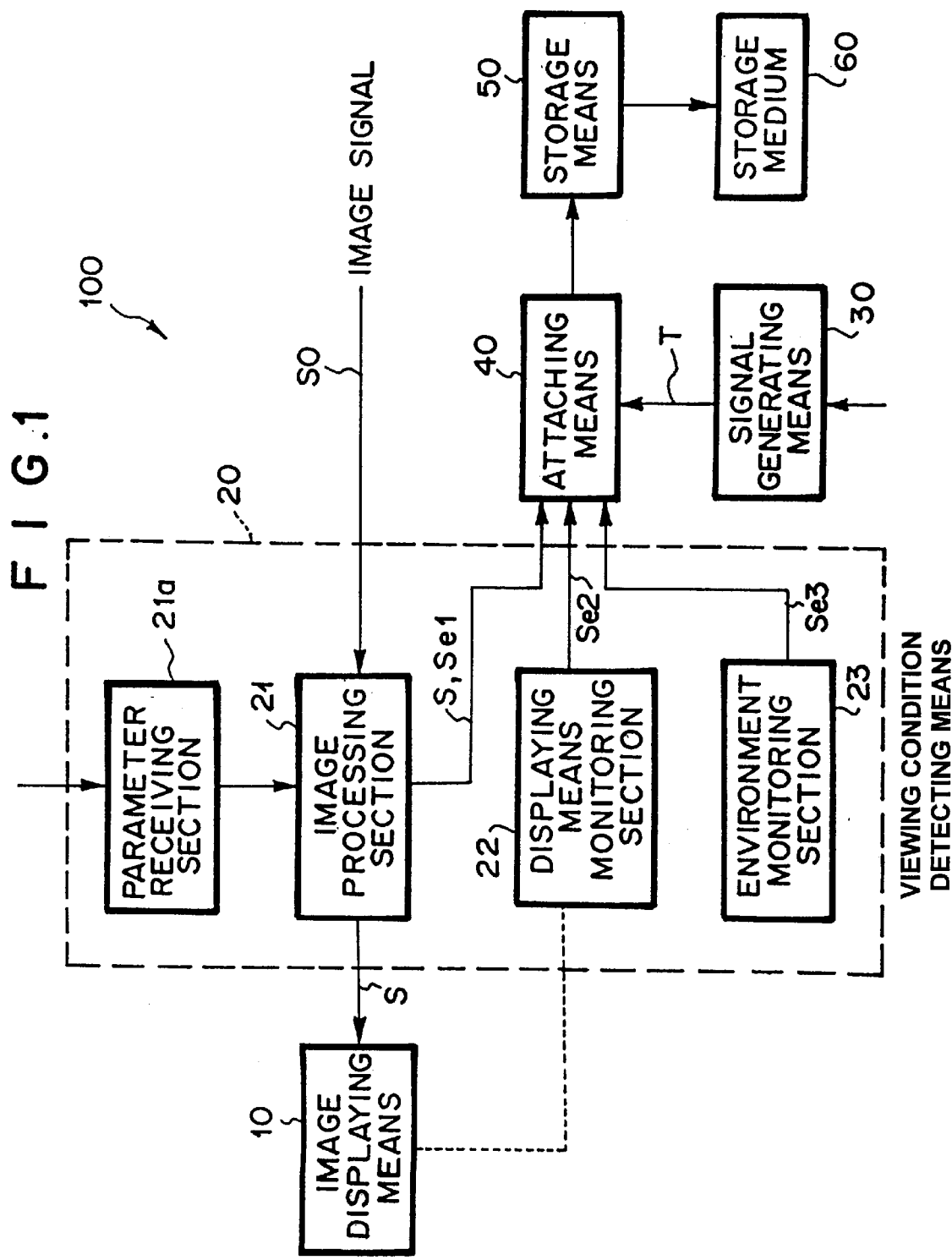

In FIG. 1, a diagnostic image information storing apparatus 100 in accordance with an embodiment of the present invention comprises an image displaying means 10 which displays a visible image on the basis of an image signal S input thereinto, a viewing condition detecting means 20 which detects information Se on the viewing condition of the image displayed by the image displaying means 10, a storage instruction signal generating means 30 which generates a storage instruction signal T, which commands that information is to be stored, in response to a signal from an operator representing that the image currently displayed by the image displaying means is used for a diagnosis, an attaching means 40 which attaches the information Se on the viewing condition detected by the viewing condition detecting means 20 upon generation of the storage instruction signal T to the image signal S, and a storage means 50 which stores the image signal S attached with the information Se on the viewing condition in a storage medium 60 such as an optical disc.

The viewing condition detecting means 20 comprises an image processing section 21 which carries out an image processing according to image processing parameters on an original image signal SO input into the image processing section 21, a displaying means monitoring section 22 which monitors the image displayed by the image displaying means 10 and detects the displaying properties Se2 of the image displaying means 10 itself, and an environment monitoring section 23 which detects the condition of environment Se3 in which the image displaying means 10 stands.

The image processing section 21 is provided with a parameter receiving section 21a which receives parameters on the image from the operator and carries out a gradation processing, a frequency processing, an enlargement/contraction processing, a gradation correction processing of the image display system 10 and the like on the original image signal SO according to image processing parameters. The image processing section 21 inputs the processed image signal S into the image displaying means 10 and inputs the image processing parameters as representing the condition of the image processing Se1 into the attaching means 40.

The original image signal SO is, for instance, an image signal representing radiation image obtained by a computed radiography (CR) system or the like, and may be either an image signal which has been subjected to a predetermined gradation processing, frequency processing and the like or an image signal as read out from a stimulable phosphor sheet or the like.

The displaying means monitoring section 22 causes the image displaying means 10 to display a reference pattern image and monitors the reference pattern image from the exterior. Then the displaying means monitoring section 22 detects a maximum brightness, gradation, chromaticity, sharpness and noise characteristics and inputs the detected information into the attaching means 40 as the displaying properties Se2 of the image displaying means 10.

The environment monitoring section 23 comprises photodiode for detecting illuminance of the environmental light on the screen of the image displaying means 10, a means for measuring the distance between the screen surface and the viewer and a chromaticity detecting means for detecting chromaticity of the environmental light, and inputs into the attaching means 40 the detected illuminance, distance and chromaticity as the condition of environment Se3.

The operation of the diagnostic image information storing apparatus 100 of this embodiment will be described, hereinbelow.

The image processing section 21 of the viewing condition detecting means 20 outputs a reference information representing a reference pattern on the basis of which the degree of image quality is measured and the image displaying means 10 displays an image pattern according to the reference information on its screen in response to receipt of the information.

Then the displaying means monitoring section 22 monitors the reference pattern image from the exterior, and detects the displaying properties Se2 of the image displaying means 10, that is, the maximum brightness, gradation, chromaticity, sharpness and noise characteristics. The detected displaying properties Se2 of the image displaying means 10 are held by the displaying means monitoring section 22.

Then the original image signal SO representing an image to be viewed is input into the image processing section 21 of the viewing condition detecting means 20. The image processing section 21 carries out an image processing under preset default processing conditions and inputs the processed image signal S into the image displaying means 10. The image displaying means 10 displays a visible image on the basis of the processed image signal S.

The operator views the displayed image and inputs image processing parameters corresponding to a desired image quality into the parameter receiving section 21a in order to improve the readability of the visible image. The image processing parameter may be input as a value representing a desired sharpness, scale or the like, or may be input, for instance, by pushing a button for changing sharpness, smoothness or the like stepwise.

The image processing parameters input into the parameter receiving section 21a are input into the image processing section 21 and the image processing section 21 carries out additional image processing according to the image processing parameters on the image signal S.

The image signal S subjected to the additional image processing is then input into the image displaying means 10 and reproduced as a visible image.

The operator views the visible image displayed by the image displaying means 10, and changes the parameters input into the parameter receiving section 21a on the basis of trial and error until a desired image quality is obtained.

The image processing section 21 carries out the additional image processing each time the parameters are changed, and accordingly the visible image displayed by the image displaying means 10 is changed each time.

The environment monitoring section 23 keeps detecting illuminance of the environmental light on the screen of the image displaying means 10, measuring the distance between the screen surface and the viewer and detecting chromaticity of the environmental light while the parameters are being changed.

When the operator determines that the visible image displayed by the image displaying means 10 comes to be of a desired quality suitable for diagnosis, the operator inputs a signal, representing that the image currently displayed by the image displaying means 10 is used for a diagnosis, into the storage instruction signal generating means 30, for instance, by pressing a predetermined switch. The storage instruction signal generating means 30 inputs a storage instruction signal T, which commands that information is to be stored, into the attaching means 40 upon receipt of the signal.

The attaching means 40 receives the condition of environment Se3 (that is, illuminance of the environmental light, the distance between the screen surface and the viewer, and chromaticity of the environmental light) detected by the environment monitoring section 23 at the time the storage instruction signal T is input, the displaying properties Se2 of the image displaying means 10 held by the displaying means monitoring section 22 at the time the storage instruction signal T is input, and the information representing the visible image which is being displayed by the image displaying means 10 at the time the operator inputs the signal representing that the image currently displayed by the image displaying means 10 is used for a diagnosis, that is, the image signal S which has been subjected to the image processing under the preset default processing conditions and the image processing parameters (the condition of the image processing) Se1 representing the additional image processing. Then the attaching means 40 attaches the information Se on the viewing condition including the condition of the image processing Se1, the displaying properties Se2 and the condition of environment Se3 to the image signal S.

The image signal S attached with the information Se on the viewing condition is input into the storage means 50 and stored in the storage medium 60.

As can be understood from the description above, in the diagnostic image information storing apparatus 100 of this embodiment, since the information Se on the viewing condition at the time a diagnosis is made is stored together with the image signal S as supplementary information, the image on the basis of which a diagnosis is made can be reproduced later with the same image quality, impression and the like, judgment upon the diagnosis can be confirmed later and fluctuation in the result of diagnosis due to change in the viewing condition can be avoided.

Though, in the embodiment described above, the information Se on the viewing condition includes the condition of the image processing Se1, the displaying properties Se2 and the condition of environment Se3, the information Se on the viewing condition need not include all of them. For example, when the environment in which the image displaying means 10 stands is kept unchanged, the information Se on the viewing condition need not include the condition of environment Se3. Further when the operator will carry out no additional image processing or cannot carry out additional image processing, the information Se on the viewing condition need not include the condition of the image processing Se1.

Further information on factors which can affect the viewing condition other than the condition of the image processing Se1, the displaying properties Se2 and the condition of environment Se3 may be included in the information Se on the viewing condition.

Though, in the embodiment described above, the information Se on the viewing condition including the condition of the image processing Se1 which the user carries out additionally is attached to the image signal S which has been subjected to the image processing under the preset default processing conditions, the information Se on the viewing condition including both the condition of the image processing Se1 which the user carries out additionally and the default processing conditions may be attached to the original image signal SO before the image processing under the preset default processing conditions.

What is claimed is:

1. A method of storing, in a predetermined storage medium, a diagnostic image which is displayed on an image display system and on the basis of which a diagnosis is made, said method comprising the steps of:

storing the diagnostic image in the predetermined storage medium; and storing information on the viewing condition of the diagnostic image displayed on the image display system in the predetermined storage medium together with the diagnostic image, wherein said viewing condition is one of an image display condition specified by a user who views the diagnostic image on the image display system, a displaying property of the image display system, or a condition of environment surrounding the image display system.

2. A method as defined in claim 1 wherein the step of storing said information on the viewing condition includes selecting at least one of a condition of the image processing which is additionally carried out when said diagnostic image is displayed by the image displaying system, the displaying property of the image display system and the condition of environment of the image display system.

3. A diagnostic image information storing apparatus comprising an image displaying means which displays a diagnostic image and a storage means which stores, in a predetermined storage medium, the diagnostic image displayed by the image displaying means, said apparatus comprising:

a viewing condition detecting means for detecting information on the viewing condition of the diagnostic image;

a storage instruction signal generating means for generating a storage instruction signal, which commands that the diagnostic image is to be stored, in response to a signal from a user; and an attaching means for attaching the information on the viewing condition detected by the viewing condition detecting means to the diagnostic image in response to the storage instruction signal, prior to said storage means storing the diagnostic image with the information on the viewing condition in said storage medium, wherein said viewing condition is one of: an image display condition specified by the user who views the diagnostic image on the image display system, a displaying property of the image display system, or a condition of environment surrounding the display system.

4. An apparatus as defined in claim 3 wherein said viewing condition detecting means further comprises means for detecting information on at least one of a condition of image processing which is additionally carried out when said diagnostic image is displayed by the image displaying means, the displaying property of the image displaying means, and the condition of environment of the image displaying means.

5. A method of storing diagnostic image information in a predetermined storage medium, the diagnostic image information representing a diagnostic image which is displayed on an image display system, said method comprising the steps of:

storing the diagnostic image information in the predetermined storage medium;

selecting displaying properties of the image display system, said displaying properties comprising at least one of maximum brightness, gradation, chromaticity, sharpness, and noise characteristics of the image display system; and storing the displaying properties of the image display system in the predetermined storage medium together with the diagnostic image information, wherein said displaying properties are specified by a user who views the diagnostic image on the image display system.

6. A method as defined in claim 5, wherein said first storing step comprises storing the diagnostic image itself in the predetermined storage medium, and wherein said second storing step comprises storing the displaying properties of the image display system in the predetermined storage medium together with the diagnostic image.

7. A diagnostic image information storing apparatus comprising an image displaying means which displays a diagnostic image and a storage means which stores, in a predetermined storage medium, diagnostic image information representing the image displayed by the image displaying means, said apparatus comprising:

a viewing condition detecting means for detecting information on displaying properties of the image displaying means, said displaying properties comprising at least one of maximum brightness, gradation, chromaticity, sharpness, and noise characteristics of the image displaying means;

a storage instruction signal generating means for generating a storage instruction signal, which commands that the image information is to be stored, in response to a signal from a user; and an attaching means for attaching the displaying properties information detected by the viewing condition detecting means to the diagnostic image information in response to the storage instruction signal, prior to said storage means storing the diagnostic image information together with the displaying properties information in said predetermined storage medium, wherein said displaying properties are specified by the user who views the diagnostic image on the image display system.

8. An apparatus as defined in claim 7, wherein said storage means stores the diagnostic image itself together with the displaying properties information in the predetermined storage medium.

9. A method of storing diagnostic image information in a predetermined storage medium, the diagnostic image information representing an image, which is displayed on an image display system, said method comprising the steps of:

storing the diagnostic image information in the predetermined storage medium;

selecting a condition of environment of the image display system, said condition of environment comprising at least one of illuminance, chromaticity of environmental light, and a distance between a user and the image display system; and storing the condition of environment in the predetermined storage medium together with the diagnostic image information.

10. A method as defined in claim 9, wherein said first storing step comprises storing the diagnostic image itself in the predetermined storage medium, and wherein said second storing step comprises storing the condition of environment of the image display system in the predetermined storage medium together with the diagnostic image.

11. A diagnostic image information storing apparatus comprising an image displaying means which displays a diagnostic image and a storage means which stores, in a predetermined storage medium, image information representing the diagnostic image displayed by the image displaying means, said apparatus comprising:

a viewing condition detecting means for detecting information on a condition of environment of the image displaying means, said condition of environment comprising at least one of illuminance, chromaticity of environmental light, and a distance between a user and the image displaying means;

a storage instruction signal generating means for generating a storage instruction signal, which commands that the image in formation is to be stored, in response to a signal from the user; and an attaching means for attaching the condition of environment information detected by the viewing condition detecting means to the diagnostic image information in response to the storage instruction signal, prior to said storage means storing the diagnostic image information together with the condition of environment information in said predetermined storage medium.

12. An apparatus as defined in claim 11, wherein said storage means stores the diagnostic image itself together with the condition of environment information in the predetermined storage medium.

13. A method of storing, in a predetermined storage medium, diagnostic image information representing a diagnostic image which is displayed on an image display system and on the basis of which a diagnosis is made, said method comprising the steps of:

storing the diagnostic image information in the predetermined storage medium;

selecting an image processing condition of the image displayed on the image display system, said image processing condition comprising at least one of a gradation processing, a frequency processing, an enlargement processing, a contraction processing, and a gradation correction processing of the image, wherein said image processing condition is specified by a user who views the diagnostic image on the image display system; and storing the image processing condition of the diagnostic image in the predetermined storage medium together with the diagnostic image information.

14. A method as defined in claim 13 wherein said first storing step comprises storing the diagnostic image itself in the predetermined storage medium, and wherein said second storing step comprises storing the image processing in the predetermined storage medium together with the diagnostic image.

15. A diagnostic image information storing apparatus comprising an image displaying means which displays a diagnostic image and a storage means which stores, in a predetermined storage medium, diagnostic image information representing the diagnostic image displayed by the image displaying means, said apparatus comprising:

a viewing condition detecting means for detecting information on an image processing condition of the diagnostic image displayed by the image displaying means, said image processing condition comprising at least one of a gradation processing, a frequency processing, an enlargement processing, a contraction processing, and a gradation correction processing of the image, wherein said image processing condition is specified by a user who views the diagnostic image on the image display system;

a storage instruction signal generating means for generating a storage instruction signal, which commands that the diagnostic image information is to be stored, in response to a signal from the user; and an attaching means for attaching the image processing condition information detected by the viewing condition detecting means to the diagnostic image information in response to the storage instruction signal, prior to said storage means storing the diagnostic image information with the image processing condition information in said storage medium.

16. An apparatus as defined in claim 15, wherein said storage means stores the diagnostic image itself together with the image processing condition information in the predetermined storage medium.

\* \* \* \* \*